(12) United States Patent
Juadjur

(10) Patent No.: US 11,865,131 B2
(45) Date of Patent: Jan. 9, 2024

(54) ANTHOCYANIN POWDER EXTRACT AND PROCESS FOR PRODUCTION

(71) Applicant: Deutsches Institut für Lebensmitteltechnik e.V., Quakenbrück (DE)

(72) Inventor: Andreas Juadjur, Quakenbrück (DE)

(73) Assignee: Deutsches Institut für Lebensmitteltechnik e.V., Quakenbrück (DE)

( * ) Notice: Subject to any disclaimer, the term of this patent is extended or adjusted under 35 U.S.C. 154(b) by 96 days.

(21) Appl. No.: 17/526,296

(22) Filed: Nov. 15, 2021

(65) Prior Publication Data

US 2022/0160740 A1    May 26, 2022

(30) Foreign Application Priority Data

Nov. 20, 2020  (DE) .......................... 102020214647.0

(51) Int. Cl.
*A61K 31/7048* (2006.01)
*A61K 9/14* (2006.01)
*A61K 31/198* (2006.01)
*A61K 36/185* (2006.01)

(52) U.S. Cl.
CPC ............ *A61K 31/7048* (2013.01); *A61K 9/14* (2013.01); *A61K 31/198* (2013.01); *A61K 36/185* (2013.01); *A61K 2236/333* (2013.01); *A61K 2236/51* (2013.01); *A61K 2236/53* (2013.01)

(58) Field of Classification Search
None
See application file for complete search history.

(56) References Cited

U.S. PATENT DOCUMENTS

2008/0063689 A1    3/2008 Farber
2011/0263834 A1   10/2011 Lees et al.

FOREIGN PATENT DOCUMENTS

CN     110731982 A  *  1/2020
WO     2014066471 A1    5/2014

OTHER PUBLICATIONS

Arakawa et. al. (The effects of arginine on protein binding and elution in hydrophobic interaction and ion-exchange chromatography, Protein Expr Purif. Jul. 2007, 54(1):110-6) (Year: 2007).*
CN-110731982-A translated doc (Year: 2020).*
Lee et al., "Determination of Total Monomeric Anthocyanin Pigment Content of Fruit Juices, Beverages, Natural Colorants, and Wines by the pH Differential Method: Collaborative Study", Journal of AOAC International, 2005, pp. 1269-1278, vol. 88, No. 5, Oxford University Press.
Juadjur et al., "Development of a Novel Adsorptive Membrane Chromatographic Method for the Fractionation of Polyphenols from Bilberry", Journal of Agricultural and Food Chemistry, 2012, pp. 2427-2433, vol. 60, ACS Publications.
Esatbeyoglu et al., "Fractionation of Plant Bioactives from Black Carrots (*Daucus carota* subspecies *sativus* varietas *atrorubens Alef.*) by Adsorptive Membrane Chromatography and Analysis of Their Potential Anti-Diabetic Activity", Journal of Agricultural and Food Chemistry, 2016, pp. 5901-5908, vol. 64, ACS Publications.

* cited by examiner

*Primary Examiner* — Aaron J Kosar
*Assistant Examiner* — Jacob A Boeckelman
(74) *Attorney, Agent, or Firm* — Greer, Burns & Crain, Ltd.; Steven P. Fallon

(57) ABSTRACT

The present invention relates to a process for producing an extract powder from a fruit material of e.g. berry fruits, wherein anthocyanins are enriched from the fruit material, and to the product obtainable by the process. In the process according to the invention, anthocyanins are enriched via a cation exchanger. By eluting the anthocyanins from the cation exchanger by means of L-arginine, the process has the advantage that no salt needs to be purified from the eluate to produce an extract powder suitable for use as a dietary supplement.

13 Claims, 1 Drawing Sheet

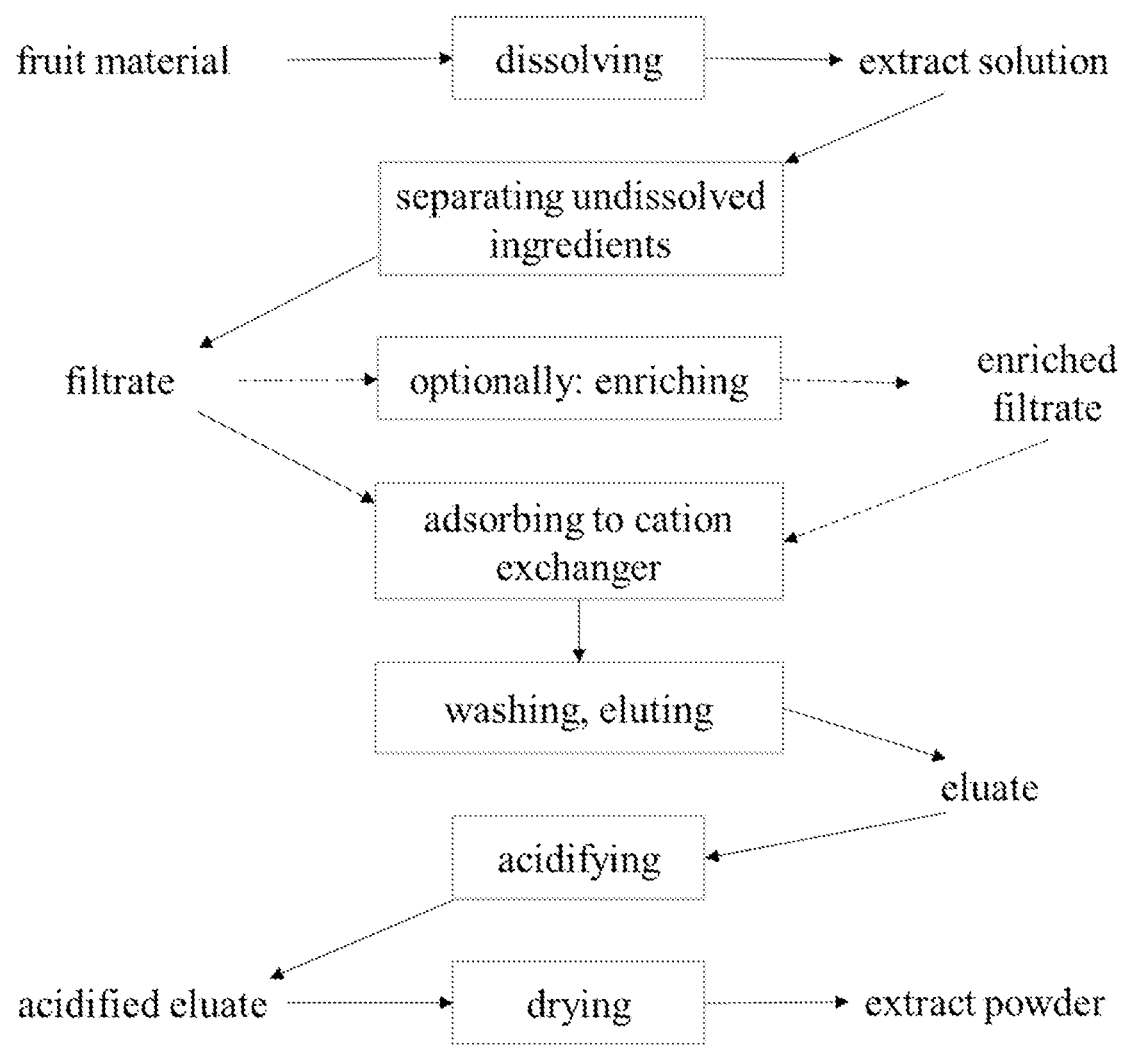

ANTHOCYANIN POWDER EXTRACT AND PROCESS FOR PRODUCTION

The present invention relates to a process for producing an extract powder from a fruit material, e.g. berry fruit, by which anthocyanins are enriched from the fruit material, and to the product obtainable by the process.

The process has the advantage that anthocyanins from fruit material can be enriched to a higher level than by other processes, since the anthocyanins are separated from uncharged polyphenols. By using natural fruit material, the process has the advantage that the anthocyanins are present in their natural composition in the extract powder.

The extract powder obtainable by the process according to the invention is suitable for use as dietary supplement for long-term lowering and stabilization of the blood pressure and for prevention of cardiovascular diseases, for supportive treatment of chronic inflammatory bowel diseases such as Crohn's disease, for improved blood circulation and regeneration during and after strength training, and for support in erectile dysfunction (especially in combination with L-arginine).

STATE OF THE ART

From Juadjur, A., Winterhalter, P., J. Agric. Food Chem. 2012, 60, 10, 2427-2433, it is known to enrich anthocyanins by means of cation exchangers, e.g. by means of membrane chromatography on Sartobind S membranes.

This process has the disadvantage that salt has to be separated in an additional step to produce an extract having an acceptable salt content, and it therefore does not allow the production of anthocyanin-containing extract powder cheaply on a large scale.

Jiao et al, Emirates Journal of Food and Agriculture, Vol. 29, no. 8, August 2017, pp. 581-8 describes a process for extracting anthocyanins from fruits by adsorption on Amberlite XAD-7. The maximum anthocyanin content achieved in the extract produced by the process is 36 wt.-%.

This process has the disadvantage that the extract in addition to anthocyanins contains other polyphenols.

WO 2014/066471 A1 describes a multimodal resin for the purification of proteins and nucleic acids, with elution by means of Good's buffer and ethylene glycol or propylene glycol.

US 2011/0263834 A1 describes processes for separating impurities from culture supernatants after fermentation via a cation exchanger. The wash buffer can contain arginine in combination with sodium phosphate and sarcosine, elution is carried out with table salt.

Esatbeyoglu et al, J Agric. Food Chem, 2016, Vol. 64, pp. 5901-5908, describes the extraction and fractionation of anthocyanins from carrots by means of an XAD-7 column and subsequently a Sartobind S membrane. The extraction is carried out with a mixture of methanol/acetic acid, and the elution is carried out with table salt and methanol, wherein the table salt is subsequently separated.

US 2008/0063689 A1 describes dietary supplements containing anthocyanins and creatine. A manufacturing process is not described.

OBJECT OF THE INVENTION

The invention has the object of providing an alternative process for producing an anthocyanin-containing extract powder, and in particular of providing a process by which anthocyanins in the extract powder are enriched to 60 to 90 wt.-%. A preferred object of the invention is to provide a process for producing an extract powder comprising 60 to 90 wt.-% anthocyanins without removing salt, and the extract powder obtainable therewith.

DESCRIPTION OF THE INVENTION

The invention achieves the object by the features of the claims and in particular provides a process for producing an extract powder, the process comprising or consisting of the steps of
a. dissolving a fruit material containing anthocyanins in a solvent to produce an extract solution,
b. separating undissolved ingredients from the extract solution to produce a filtrate, optionally enriching polyphenols from the filtrate to produce an enriched filtrate,
c. adsorbing the filtrate or enriched filtrate to a cation exchanger,
d. washing the cation exchanger with a first wash solution,
e. eluting the anthocyanins from the cation exchanger with a first elution solution comprising L-arginine in aqueous alcoholic solution to produce an eluate containing anthocyanins,
f. acidifying the eluate to produce an acidified eluate, and
g. drying the acidified eluate to produce the extract powder.

In the process according to the invention, anthocyanins are enriched via a cation exchanger. By eluting the anthocyanins from the cation exchanger by means of L-arginine, the process has the advantage that no salt needs to be depleted from the eluate, e.g. in a separate process step, in order to produce an extract powder suitable for use as a dietary supplement. This results in the further advantage that anthocyanin-containing extract powder can be produced by the process on a large scale from at least 150 kg of fruit material per batch more cheaply than with known processes.

For its use as a food supplement containing L-arginine, the extract powder according to the invention has the advantage that it comprises anthocyanins in higher concentration than processes known from the prior art and that it already comprises the semi-essential amino acid L-arginine such that this does not have to be added in a step following the process.

By salt, generally those salts are understood that are suitable for the elution of anthocyanins from a cation exchanger, but in particular the salts of monovalent alkali metals such as e.g. sodium and potassium salts, especially table salt.

The fruit material can comprise whole and/or comminuted fruits, or can be a juice or pressed juice, or can e.g. be a fruit extract. Preferably, the fruit material is a pomace. Generally, the fruit material is from anthocyanin-containing fruits, such as e.g. berry fruits, berries, grapes, and/or red cabbage.

In the embodiment comprising enriching polyphenols from the filtrate, the fruit material can have a high content of cationic impurities, e.g. the fruit material can comprise or consist of pomegranates, blueberries, elderberries, and/or blackberries. Cationic impurities are natural and/or added plant-based and/or non-plant-based cationic ingredients that are not anthocyanins or flavylium cations, e.g. potassium ions. The high content of these cationic impurities is preferably a content of at least 500 mg/L or 500 mg/kg of cationic impurities, or a content at least as high as the content of anthocyanins in the fruit material. It has shown that by the process according to the invention, by the step of enriching the polyphenols from the filtrate, anthocyanins can be concentrated to a higher degree than by other processes, even from fruit material having a high content of cationic impurities.

The dissolving of the fruit material in the solvent comprises dissolving the anthocyanins contained in the fruit material and optionally dissolving further ingredients of the fruit material in the solvent.

The solvent is a polar, preferably an aqueous alcoholic solution. More preferably, the solvent consists of 19 parts by volume of primary alcohol and 1 part by volume of acid, e.g. concentrated acetic acid.

In the embodiment in which the fruit material is a juice, dissolving of the fruit material can be carried out by adding acid to the fruit material so that the extract solution consists of acidified fruit material and preferably has a pH value of at least 2 up to 4. In this embodiment, the solvent is preferably an aqueous acidic solution, preferably having a pH value of 2, and more preferably can consist of distilled water and HCl. At a pH value of 2, anthocyanins are present as stable flavylium cations and can bind to a cation exchanger.

The dissolving of the fruit material can be carried out by mixing, e.g. stirring or resuspending in the solvent to produce an extract solution. Optionally, the dissolving can comprise heating the solvent up to 40° C., e.g. up to 35° C.

Further optionally, the dissolving can comprise digesting cells in the fruit material, e.g. by adding cell structure digesting enzymes, e.g. enzymes having pectinase, glucanase, pentosanase, and/or hemicellulase activity, and/or by applying a pulsed electric field (PEF), e.g. having a field strength of at least 1 kV/cm up to 4 kV/cm and an energy input of at least 10 kJ/kg up to 30 kJ/kg, and/or by applying ultrasound, e.g. of a frequency of at least 20 kHz up to 40 kHz at an intensity of e.g. 0.5 W/cm$^2$ for at least 10 minutes up to 60 minutes, and/or by mechanically pressing the fruit material. It has shown that by the process, after digesting the cells in the fruit material a higher yield of anthocyanins in the extract powder can be achieved.

Generally, the primary alcohol is a branched or unbranched alcohol and has a chain length of C1 to C10, i.e. 1 to 10 carbon atoms. In particular, the primary alcohol is selected from the group comprising methanol, ethanol, 1-propanol, 1-butanol, 1-pentanol, or mixtures thereof. The primary alcohol is preferably free of denaturing agents and further preferably free from water.

Optionally, the primary alcohol is a primary alcohol suitable for use as food, i.e. ethanol.

Generally, the acid is an aqueous, preferably concentrated aqueous solution of at least one compound selected from the group comprising acetic acid, hydrochloric acid, citric acid, phosphoric acid, fumaric acid, ascorbic acid or oxalic acid. For example, the acid can be concentrated acetic acid (glacial acetic acid, at least 99 wt.-% in water, corresponding to approx. 18 mol/L), or concentrated hydrochloric acid HCl (37 wt.-% in water, corresponding to approx. 12 mol/L), or concentrated phosphoric acid (89 wt.-% in water, corresponding to approx. 16 mol/L). Preferably, the acid is suitable for food, in particular selected from concentrated acetic acid, concentrated citric acid, concentrated ascorbic acid, concentrated malic acid, or concentrated tartaric acid, preferably having a pK$_s$ value of at most 5, more preferably of at most 4 or of at most 3.

Preferably, in the process in step a., the same acid is added to the fruit material as in step f. to the eluate.

Prior to separating the ingredients in the cation exchanger, undissolved ingredients of the extract solution, such as e.g. fruit pulp or pomace residues, in step b. of the process are separated from the extract solution, e.g. by filtration and/or centrifugation and/or decanting, to produce a filtrate. Undissolved ingredients hinder the production of the extract powder by clogging the cation exchanger so that the anthocyanins cannot be enriched or can only be enriched to a lesser extent.

In the embodiment in which the separating of the undissolved ingredients from the extract solution is carried out by filtration, the filter is generally set up to separate undissolved ingredients such as e.g. fruit pulp or pomace residues from the extract solution. The filter is preferably a filter made of polyethersulfone (PES) or polyethylene terephthalate (PET) and has a pore size of at most 0.45 µm, preferably of at most 0.2 µm. In this embodiment, the separation optionally encompasses several filtration steps, wherein the first filtration step is carried out with a first filter having a pore size of at least 10 µm or at least 50 µm, and the filtrate is further filtered in at least one further filtration step through at least one subsequent filter, wherein the at least one subsequent filter preferably has a smaller pore size than the first filter, e.g. at most 3 µm or at most 0.45 µm, preferably at most 0.2 µm. The filter can be regenerated after filtration, e.g. by rinsing with an aqueous solution comprising at least 0.1 M, preferably at least 1 M NaOH, optionally in reverse flow direction.

Adsorbing of the filtrate or enriched filtrate to a cation exchanger is preferably carried out by overflowing the cation exchanger with the filtrate. Cationic ingredients of the filtrate, e.g. the anthocyanins contained in the filtrate or cationic impurities such as e.g. potassium ions, therein by ionic interactions interact with the terminal anionic groups of the cation exchanger, which are e.g. sulfonic acid groups or carboxy groups.

Preferably, the cation exchanger is arranged as a bulk of a stationary chromatographic phase or in a flow-through column in a fixed manner. Further preferably, the cation exchanger is formed as a membrane adsorber. The cation exchanger is also referred to as first ion exchanger.

Those ingredients of the filtrate, such as e.g. phenolic acids or flavonoids, that do not bind to the cation exchanger are flushed from the cation exchanger as a flow-through in step c. of the process. Optionally, the flow-through is collected as permeate. Further optionally, the permeate is dried, preferably freeze-dried, to produce a permeate powder. The drying of the permeate can comprise evaporating the solvent, e.g. by means of a rotary evaporator or by fluidized bed drying, and/or can comprise vacuum drying at maximally 40° C., preferably maximally 35° C., and/or freeze-drying. Preferably, the drying is carried out at a temperature of at most −10° C. and an absolute pressure of at most 10 mbar absolute. Phenolic acids and/or flavonoids are enriched in the permeate. The permeate powder, obtainable e.g. by drying the permeate, can e.g. be used as a food supplement.

The washing of the cation exchanger with the filtrate adsorbed thereto is carried out with a first wash solution. Therein, the ingredients of the filtrate that bind weakly or non-specifically to the cation exchanger are displaced from the cation exchanger.

The first wash solution contains a primary alcohol and an acid. Preferably, the first wash solution consists of 19 parts by volume of the primary alcohol, e.g. ethanol or methanol, and 1 part by volume of acid, e.g. concentrated acetic acid.

The anthocyanins contained in the filtrate are eluted from the cation exchanger to produce an eluate. To this end, a first elution solution which comprises L-arginine is loaded onto the cation exchanger. The L-arginine, which is cationic at acidic and neutral pH value, displaces the anthocyanins from the cation exchanger so that they are flushed from the cation exchanger as eluate.

The first elution solution comprises L-arginine in aqueous alcoholic solution. Preferably, the first elution solution is a mixture of equal volume proportions of an aqueous solution of L-arginine and a primary alcohol.

The aqueous solution of L-arginine contains L-arginine at a concentration of at least 5 mM, preferably at least 10 mM up to 1000 mM, preferably up to 500 mM, e.g. 50 mM or 100 mM and is preferably adjusted to a pH value between 2 and 7, preferably to a pH value of 4.5, by acidification, e.g. by addition of HCl or concentrated acetic acid. It has shown that under neutral and acidic conditions at a pH value between 7 and 2, L-arginine is present as a zwitterion having a positively charged guanidino group and a negatively charged acid group, and therefore has an eluting power at least equivalent to salt solutions comprising monovalent cations $K^+$ or $Na^+$ of the same concentration.

The cation exchanger can e.g. be regenerated by overflowing with an aqueous solution of sodium hydroxide (NaOH), e.g. 0.1 M NaOH, preferably 1 M NaOH, and preferably subsequent overflowing with distilled water or . . . . By the regeneration, the substances present on the cation exchanger after elution are removed, so that the cation exchanger is again ready for carrying out the process.

Optionally, prior to step c., the process additionally comprises the step of enriching the polyphenols from the filtrate produced in step b. to produce an enriched filtrate. Generally, the enriching is carried out by means of a process suitable for separating the polyphenols contained in the filtrate from other ingredients of the filtrate, e.g. from sugars, fruit acids and salts. Therein, the process is preferably a chromatography process, e.g. adsorption chromatography on Amberlite XAD-7, and is carried out by means of a chromatography column that can be flowed through, e.g. by means of a column for hydrophobic interaction chromatography (HIC column).

It has shown that an extract powder obtainable by the process of the invention from enriched filtrate has a higher content of anthocyanins and a lower content of cationic impurities than an extract powder from non-enriched filtrate.

In this embodiment, the process has the additional advantage that a high yield of anthocyanins and a high concentration of anthocyanins in the extract powder obtainable by the process can also be obtained from fruit material having a high content of cationic impurities. The fruit material is then preferably selected from pomegranates, blueberries, elderberries and/or blackberries. Alternatively, according to the invention, a higher yield of anthocyanins and a higher concentration of anthocyanins in the extract powder can be achieved than by other extraction processes if the fruit material has a content of at least 500 mg/L or 500 mg/kg of cationic impurities.

In detail, the optional step of enriching the polyphenols comprises the substeps of adsorbing the filtrate to a chromatography column, washing with a second wash solution, eluting the enriched filtrate with a second elution solution, and collecting the enriched filtrate, wherein the second wash solution is preferably an aqueous solution containing 1 vol. % acid, e.g. concentrated acetic acid, and further preferably has a pH value of 2.8, and wherein the second elution solution is preferably primary alcohol+1 vol. % acid, e.g. concentrated acetic acid. Therein, during washing, the sugars and salts remaining in the filtrate are displaced from the chromatography column, and during elution, the anthocyanins and optionally polyphenols are eluted from the chromatography column as an enriched filtrate.

The subsequent steps c. to g. of the process can be carried out with the optionally prepared enriched filtrate in the same way as with the filtrate prepared in step b.

The eluate is acidified by adding acid, preferably 1 vol. % acid, more preferably 1 vol. % concentrated acetic acid, to produce an acidified eluate. It has shown that cationic flavylium salts of anthocyanins, e.g. acetate salts or chloride salts, are more storage-stable than anthocyanins which are not present as a cation, but e.g. uncharged or in deprotonated anionic form.

The drying of the acidified eluate to produce the extract powder of the invention can be carried out in a fluidized bed dryer or in a spray dryer and/or jet tower dryer, or can e.g. be carried out in a freeze-drying apparatus. The drying of the acidified eluate can comprise the step of evaporating the elution solution (primary alcohol, e.g. ethanol or methanol), e.g. by means of an evaporator, or can alternatively or additionally comprise a step of vacuum drying at maximally 40° C., preferably maximally 35° C., and/or freeze-drying. Preferably, the drying is carried out at a temperature of at most −10° C. and at an absolute pressure (vacuum) of at most 10 mbar absolute.

The extract powder according to the invention preferably has a residual moisture of at most 1%, preferably at most 0.1%, and more preferably is free of water and primary alcohol.

The extract powder according to the invention, and obtainable by the process, is characterized by an anthocyanin content of at least 60 wt.-%, preferably at least 70 wt.-% up to 90 wt.-%, preferably up to 85 wt.-%, e.g. 80 wt.-%, and an L-arginine content of at least 5 wt.-%, preferably at least 10 wt.-% up to 30 wt.-%, preferably up to 25 wt.-%, e.g. 20 wt.-%. Preferably, an extract powder according to the invention has a salt content of at most 5 wt.-%, preferably at most 3 wt.-% or at most 2 wt.-%, e.g. 0.5 wt.-%, or is free of salt. An extract powder according to the invention can e.g. comprise 80 wt.-% of anthocyanins and 20 wt.-% of L-arginine and be free of salt.

The extract powder preferably comprises the natural anthocyanins contained therein in their natural composition and while maintaining the natural anthocyanin profile of the fruit material, i.e. in the same proportions to one another as in the fruit material. Since typical anthocyanin contents of fresh blueberries are between 0.5 and 1 wt.-%, this corresponds to a 60- to 180-fold enrichment of anthocyanins compared to the content of fresh fruit. Thus, the anthocyanin content in 250 mg of the extract, taken as a dietary supplement, corresponds approximately to the anthocyanin content of 25 to 50 g of fresh blueberries.

In a preferred embodiment of the process, all buffers and solutions used therein are suitable for food, i.e. preferably the solvent consists of 19 parts by volume ethanol and 1 part by volume acid, the first wash solution consists of 19 parts by volume ethanol and 1 part by volume acid, the optional second wash solution consists of 1 vol. % acid in water, the first elution solution consists of an aqueous solution of L-arginine mixed in equal parts by volume with ethanol, the optional second elution solution consists of 1 vol. % acid in ethanol, and the acid is selected from concentrated acetic acid, concentrated citric acid, concentrated ascorbic acid, concentrated phosphoric acid, concentrated malic acid or concentrated tartaric acid.

The invention will now be described in more detail with reference to an example and with reference to the FIGURE, which shows a schematic overview of the process steps.

The FIGURE shows a schematic overview of the process according to the invention, which comprises the steps of
a. dissolving a fruit material containing anthocyanins in a solvent to produce an extract solution,
b. separating undissolved ingredients from the extract solution to produce a filtrate, optionally enriching the filtrate to produce an enriched filtrate,
c. adsorbing the filtrate or enriched filtrate to a cation exchanger,
d. washing the cation exchanger with a first wash solution,
e. eluting with a first elution solution comprising L-arginine in aqueous alcoholic solution to produce an eluate containing anthocyanins,
f. acidifying the eluate by addition of acid to produce an acidified eluate, and
g. drying the acidified eluate to produce the extract powder.

Example: Production of an Extract Powder from Elderberry Juice

Elderberry juice as fruit material was produced from elderberries by mechanical pressing. 5,000 g of the fruit material was dissolved by admixing of 1 vol. % concentrated acetic acid as solvent to produce an extract solution, and was filtered through a filter unit having a pore size of 0.2 μm to produce a filtrate. Therein, undissolved ingredients were separated from the extract solution.

Polyphenols, e.g. anthocyanins, contained in the filtrate were enriched to produce an enriched filtrate. Therein, the filtrate was guided over a flow-through HIC column having a column volume of 1800 mL, filled with Amberlite XAD-7 column material (manufacturer: Sigma Aldrich). The HIC column was washed with 3 column volumes of a second wash solution made of distilled water+1 vol. % concentrated acetic acid. The enriched filtrate was eluted with 1,000 mL of a second elution solution made of ethanol+1 vol. % concentrated acetic acid to produce an enriched filtrate.

The enriched filtrate was subsequently transferred to a cation exchanger in the form of a membrane adsorber (Sartobind S, available from Sartorius, 150 mL column volume) having terminal sulfonic acid groups. Prior to this, the cation exchanger had been regenerated with 6 column volumes of an aqueous 1 M NaOH solution and had been equilibrated with 6 column volumes of 0.01 M HCL followed by 3 column volumes of an ethanolic solution containing 1 vol. % concentrated acetic acid. The cation exchanger was washed with 3 column volumes of a first wash solution containing ethanol+1 vol. % concentrated acetic acid. The elution from the cation exchanger was subsequently carried out with 800 mL of a first elution solution made of 0.02 M L-arginine in distilled water, adjusted to a pH value of 4.5 with concentrated acetic acid, mixed with an equal volume of ethanol. The first 200 mL of the elution volume was discarded as dead volume, the remaining 600 mL of the elution volume was collected as eluate. The eluate was acidified by adding 6 mL of concentrated acetic acid to produce an acidified eluate. The acidified eluate was first dried for 120 min at room temperature and a pressure of 10 mbar absolute on a rotary evaporator, and was subsequently freeze-dried in a freeze-drying apparatus (Alpha 2-4 LD plus, Christ, Osterode (Germany)) at a temperature of −83° C. and a vacuum of <0.1 mbar absolute for 48 h to produce the extract powder.

The extract powder was analyzed for cyanidin-3-glucoside equivalents by means of HPLC, was tested for its anthocyanin content by means of the pH differential process of Lee et al. (2005), and for its L-arginine content by means of LC-MS and $^1$H-NMR spectroscopy. Cyanidin-3-glucoside equivalents are the anthocyanins present in elderberries. Cyanidin-3-glucoside is the most highly concentrated anthocyanin in blackberries. This resulted in a content of cyanidin-3-glucoside equivalents, or anthocyanin content, of 80 wt.-% and a content of L-arginine of 20 wt.-%. Moreover, it showed a content of natural table salt of less than 0.3 wt.-%, measured as sodium content by means of optical emission spectroscopy.

The invention claimed is:

1. A process for producing an extract powder containing 60 to 90 wt.-% anthocyanins, 10 to 30 wt.-% L-arginine, and a salt content of at most 5 wt.-%, the process comprising the steps of
a. dissolving a fruit material containing anthocyanins in a solvent to produce an extract solution,
b. separating undissolved ingredients from the extract solution to produce a filtrate,
c. adsorbing the filtrate to a cation exchanger,
d. washing the cation exchanger with a first wash solution,
e. eluting the anthocyanins from the cation exchanger with a first elution solution to produce an eluate containing anthocyanins,
f. acidifying the eluate by adding acid to produce an acidified eluate,
g. drying the acidified eluate to produce the extract powder,
wherein the first elution solution consisting of L-arginine in aqueous alcoholic solution, wherein the first elution solution has a pH value of 4.5 and comprises L-arginine at a concentration of at least 5 mM up to 1000 mM, and wherein the first elution solution consists of an aqueous solution of L-arginine and primary alcohol mixed in equal volume proportions.

2. The process according to claim 1, consisting of the steps of
a. dissolving a fruit material containing anthocyanins in a solvent to produce an extract solution,
b. separating undissolved ingredients from the extract solution to produce a filtrate,
c. adsorbing the filtrate to a cation exchanger,
d. washing the cation exchanger with a first wash solution,
e. eluting the anthocyanins from the cation exchanger with a first elution solution to produce an eluate containing anthocyanins,
f. acidifying the eluate by adding acid to produce an acidified eluate,
g. drying the acidified eluate to produce the extract powder.

3. The process according to claim 1, consisting of the steps of
a. dissolving a fruit material containing anthocyanins in a solvent to produce an extract solution,
b. separating undissolved ingredients from the extract solution to produce a filtrate,
enriching polyphenols from the filtrate to produce an enriched filtrate, with adsorbing the filtrate to a chromatography column, washing with a second wash solution, eluting the enriched filtrate with a second elution solution, and collecting the enriched filtrate, wherein the chromatography column is a HIC column, the second wash solution is an aqueous solution containing 1 vol. % concentrated acetic acid, and the second elution solution is primary alcohol+1 vol. % concentrated acetic acid,
c. adsorbing the enriched filtrate to a cation exchanger, d. washing the cation exchanger with a first wash solution,
e. eluting the anthocyanins from the cation exchanger with a first elution solution to produce an eluate containing anthocyanins,
f. acidifying the eluate by adding acid to produce an acidified eluate,
g. drying the acidified eluate to produce the extract powder.

4. The process according to claim 3, characterized in that the fruit material has a content of at least 500 mg/L or 500 mg/kg of cationic impurities.

5. The process according to claim 1, wherein the solvent consists of 19 parts by volume of the primary alcohol and 1 part by volume of acid.

6. The process according to claim 1, wherein the solvent consists of distilled water and HCl, and the extract solution has a pH value of 2.

7. The process according to claim 1, wherein the primary alcohol is a primary alcohol suitable for use as food.

8. The process according to claim 1, wherein the separating comprises multiple filtration steps, wherein the first filtration step is carried out by a first filter having a pore size of at least 10 μm, and the filtrate is further filtered in at least one further filtration step through at least one subsequent filter, wherein the at least one subsequent filter has a smaller pore size than the first filter.

9. The process according to claim 1, wherein prior to step c. the polyphenols are enriched from the filtrate to produce an enriched filtrate, and the further steps c. to g. of the process are carried out with the enriched filtrate, wherein enriching of the polyphenols from the filtrate comprises the substeps of adsorbing the filtrate to a chromatography column, washing with a second wash solution, eluting the enriched filtrate with a second elution solution, and collecting the enriched filtrate, wherein the chromatography column is a HIC column, the second wash solution is an aqueous solution containing 1 vol. % concentrated acetic acid, and the second elution solution is primary alcohol+1 vol. % concentrated acetic acid.

10. The process according to claim 9, wherein the fruit material has a content of at least 500 mg/L or 500 mg/kg of cationic impurities.

11. The process according to claim 1, wherein the cation exchanger is formed as a membrane adsorber.

12. The process according to claim 1, wherein in step c. of the process, those ingredients of the filtrate or of the enriched filtrate which are flushed as flow-through from the cation exchanger are collected as permeate and the permeate is dried to produce a permeate powder.

13. An extract powder containing 60 to 90 wt.-% anthocyanins and 10 to 30 wt.-% L-arginine, obtained by a process according to claim 1, wherein the anthocyanins consist of a composition of natural anthocyanins of the fruit material.

* * * * *